T

US007049328B2

(12) United States Patent
Spino et al.

(10) Patent No.: US 7,049,328 B2
(45) Date of Patent: May 23, 2006

(54) USE FOR DEFERIPRONE

(75) Inventors: Michael Spino, Pickering (CA); Antonio Piga, Moncalieri (IT)

(73) Assignee: Apotex Inc., Weston (CA)

( * ) Notice: Subject to any disclaimer, the term of this patent is extended or adjusted under 35 U.S.C. 154(b) by 0 days.

(21) Appl. No.: 10/311,814

(22) PCT Filed: Jun. 28, 2001

(86) PCT No.: PCT/CA01/00956

§ 371 (c)(1),
(2), (4) Date: Apr. 4, 2003

(87) PCT Pub. No.: WO02/02114

PCT Pub. Date: Jan. 10, 2002

(65) Prior Publication Data
US 2003/0158234 A1 Aug. 21, 2003

(30) Foreign Application Priority Data
Jun. 30, 2000 (CA) .................................. 2313270

(51) Int. Cl.
A61K 31/44 (2006.01)
A61K 31/16 (2006.01)
(52) U.S. Cl. ....................... 514/348; 514/616
(58) Field of Classification Search ................ 514/348, 514/616
See application file for complete search history.

(56) References Cited

U.S. PATENT DOCUMENTS 5,922,761 A * 7/1999 Lai ............................. 514/476

OTHER PUBLICATIONS

Medline Abstract, PubMed ID: 9350180, Hoffbrand, et al., Journ. International Med. Suppl, (1997) 740 37-41.*
Medline Abstract, PubMed ID: 9414297, Hoffbrand et al., Blood, (Jan. 1, 1998), 91(1), 295-300.*
Medline Abstract, PubMed ID: 158721, Olivieri et al., Blood, (May 15, 1992), 79 (10), 2741-8.*
Anderson, Lisa J, et al., Comparison of effects of oral deferiprone and subcutaneous desferrioxamine . . . in beta-thalassaemia: Lancet 2002; 360: pp. 516-520.
Black's Law Dictionary, p. 1502.
Butler, Craig, New YorkAcademy of Sciences Symposium, The Eighth Cooley's Anemia Symposium . . . for medical professionals and patients; CAF Website; May 17, 2005.
U.S. Newswire, Cooley's Anemia Foundation Presents Symposium on Iron Overload and Cardiac Disease: New Interventions: Dec. 10, 2004.
Barnabee et al., Deferiprone Protects Against Doxorubicin-Induced Myocyte Cytotoxicity, Free Radical Biology & Medicine 2002; vol. 33, No. 2: pp. 266-275.
Hasinoff et al., The Oral Iron Chelator ICL670A (Deferasirox) Does Not Protect Myocytes Against Doxorubicin, Free Radical Biology & Medicine 2003; vol. 35, No. 11: p. 1469-1479.
Gabutti V, Piga A. Results of Long-Term Iron-Chelating Therapy. Acta Haematol 1996; 95:26-36.
Wolfe LC, Olivieri NF, Sallan D, Colan S, Rose V, Propper RD et al. Prevention of cardiac disease by subcutaneous desferrioxamine in patients with thalassemia major. N Engl J Med 1985; 312(25): 1600-1603.
Aldouri MA, Wonke B. Hoffbrand AV, Flynn DM, Ward SE, Agnew JE et al. High Incidence of Cardiomyopathy in Beta-Thalassemia Patients Receiving Regular Transfusion and Iron Chelation: Reversal by Intensified Chelation. Acta Haematol 1990; 84:113-117.
Brittenham GM, Griffith PM, Nienhuis AW, McLaren CE, Young NS, Tucker EE et al. Efficacy of Desferrioxamine in Preventing Complications of Iron Overload in Patients with Thalassemia Major. N Engl J Med 1994; 331(9):567-573.
Giardina PJV, Ehlers KH, Engle MA, Grady RW, Hilgartner MW. The Effect of Subcutaneous Desferrioxamine on the Cardiac Profile of Thalassemia Major: A Five-Year Study. Ann N Y Acad Sci 1985; 445:282-292.
Borgna-Pignatti C, Rugologgo S, DeStefano P, Piga A, et al. Survival and Disease Complications in Thalassemia Major. Ann N Y Acad Sci 1998; 850:227-231.
Olivieri NF, Nathan DG, MacMillan JH, Wayne AS, Liu P, McGee A et al. Survival in Medically Treated Patients with Homozygous Beta-Thalassemia. N Engl J Med 1994; 331(9):574-578.
Addis A, Loebstein R, Koren G, Einarson TR. Meta-analytic review of the clinical effectiveness of oral deferiprone (Deferiprone). Eur J Clin Pharmacol 1999; 55:1-6.
Grady RW, Hilgartner MW, Giardina PJV. Deferiprone: Its Effectiveness Relative to that of Desferrioxamine. 6th International Conference on Thalassemia and the Haemoglobinopathies, Abstract #2. 1997.
Olivieri NF, Brittenham GM, Armstrong SAM, Basran RK, Daneman R, Daneman N et al. First Prospective Randomized Trial of the Iron Chelators Deferiprone (Deferiprone) and Deferoxamine. Blood 86[10 Suppl. 1], 249a. 1995.
Olivieri NF, Belluzzo N, Muraca M, MacKenzie CC, Milone S, Polsinelli K et al. Evidence of Reduction in Hepatic, Cardiac and Pituitary Iron Stores in Patients with Thalassemia Major During Long-Term Therapy with the Orally Active Iron Chelating Agent Deferiprone. Blood 84[10 Suppl. 1], 109a. 1994.

(Continued)

Primary Examiner—Raymond J. Henley, III
(74) Attorney, Agent, or Firm—Neil H. Hughes; Ivor M. Hughes; Marcelo K. Sarkis

(57) ABSTRACT

A method of treating iron induced cardiac disease in a patient with iron overload, such as in thalassemia or the like comprising administering to the patient a therapeutically effective amount of deferiprone or a physiologically acceptable salt thereof sufficient to treat iron induced cardiac disease normally associated with iron overload.

20 Claims, 1 Drawing Sheet

OTHER PUBLICATIONS

Link G, Konijin AM, Hershko C. Cardioprotective effect of alpha-tocopherol, ascorbate, desferrioxamine, and deferiprone: mitochondrial function in cultured, iron-loaded heart cells. J Lab Clin Med 1999; 133: 179-188.

De Franceschi L, Shalev O, Piga A, Collell M, Olivieri O, Corrocher R et al. Deferiprone therapy in homozygous human beta-thalassemia removes erythrocyte membrane free iron and reduces KCI contransport activity. J Lab Clin Med 1999; 133:64-69.

Carthew P, Smith AG, Hider RC, Dorman B, Edwards RE, Francis JE. Potentiation of iron accumulation in cardiac myocytes during the treatment of iron overload in gerbils with the hydroxypridinone iron chelator CP94. Biometals 1994; 7:267-271.

Hider RC, Kayyli R, Evans P, Mackinnon S. The production of Hydroxyl Radicals by Deferiprone—iron compounds under physiological conditions. Blood 94[10], 406a. 1999.

Engle MA, Erlandson M, Smith CH. Late Cardiac Complications of Chronic, Severe, Refractory Anemia with Hemochromatosis. Circulation 1964; 30:698-705.

The Criteria Committee of the New York Heart Association. Nomenclature and Criteria for Diagnosis of Disease of the heart and Great Vessels. 9$^{th}$ ed. Boston, Mass; Little, Brown & Co; 1994:253-255.

Sirchia G, Zanella A. A Short Guide to the Management of Thalassemia. Thalassemia Today: the Mediterranean Experience. 1987: 635-670.

Berdoukas V, Bohans T. The Effect of Liver Iron on Cardiac Function. 10$^{th}$ International Conference on Oral Chelators in the treatment of Thalassemia and other diseases and Biomed Meeting 10, 13. 2000.

Hershko C, Graham G, Bates GW, Rachmilewitz EA. Non-Specific Serum Iron in Thalassemia: an Abnormal Serum Iron Fraction of Potential Toxicity. Br J Haematol 1978; 40: 255-263.

Olivieri NF, Koren G, Matsui D, Liu P, Blendis L, Cameron R et al. Reduction of Tissue Iron Stores and Normalization of Serum Ferritin During Treatment with the Oral Iron Chelator Deferiprone in Thalassemia Intermedia. Blood 1992; 79(10):2741-2748.

Al-Refaie FN, Sheppard L, Nortey P, Wonke B, Hoffbrand AV. Pharmacokinetics of the Oral Iron Chelator Deferiprone (Deferiprone) in Patients with Iron Overload. Br J Haematol 1995; 89:403-408.

Novartis Marketing Brochure on Desferal (Desferrioxamine). 1998. Switzerland, Novartis Pharma AG.

Grady RW, Berdoukas VA, Rachmilewitz EA, Giardina PJ. Combining Deferiprone and Desferrioxamine to optimize Chelation. 10$^{th}$ International Conference on Oral Chelators in the treatment of Thalassemia and other diseases and Biomed Meeting, Limassol, Cyprus p. 9. Mar. 2000.

Töndury P, Zimmermann A, Nielsen P, Hirt A. Liver iron and fibrosis during long-term treatment with deferiprone in Swiss thalassaemic patients. Br. J. Haematol. 1998;101(3):413-5.

Olivieri NF, Brittenham GM, McLaren CE, Templeton DM, Cameron RG, McClelland RA et al. Long-term safety and effectiveness of iron-chelation therapy with deferiprone for thalassemia major. N Engl J Med 1998; 339(7):417-423.

Hoffbrand AV, Al-Refaie FN, Davis B, Siritanakatkul N, Jackson BFA, Cochrane J et al. Long-Term Trial of Deferiprone in 51 Transfusion-Dependent Iron Overloaded Patients. Blood 1998; 91(1):295-300.

Olivieri NF, Butany J, Templeton DM, Brittenham GM. Cardiac Failure and Myocardial Fibrosis in a patient with Thalassemia Major (TM) Treated with Long-Term Deferiprone. Blood 92[10 (Suppl 1)], 532a. 1998.

Cohen AR, Galanello R, Piga A, DiPalma A, Vullo C, Tricta F. Safety profile of the oral iron chelator deferiprone: a multicentre study. Br J Haematol 2000; 108:305-312.

Agarwal MB, Rajadhyaksha G, Munot S. Deferiprone: A report of 22 patients who have taken it for over a decade. 10$^{th}$ International Conference on Oral chelators in the Treatment of Thalassemia and other Diseases and Biomed Meeting, Limassol, Cyprus, p. 3. Mar. 2000.

Liu P. Personal letter from Dr. Liu on reversal of the heart failure in a patient with thalassemia treated with deferiprone. May 13, 1996.

Ramm GA, Britton RS, Brunt EM, O'Neill R, Bacon BR. Hepatic iron overload in pathogen-free gerbils does not result in bridging fibrosis or cirrhosis. Bioiron'99, p. 327. 1999.

Hershko C., Link G., Konijn A. M. Relative effectiveness of desferrioxamine and deferiprone in protecting iron-loaded Gerbils from non-transferrin bound iron (NTBI) toxicity. Blood 94 (10): 422a; 1999.

Porter JB. Evaluation of New Iron Chelators for Clinical Use. Acta Haematol 1996; 95:13-25.

Al-Refaie FN, Hershko C, Hoffbrand AV, Kosaryan M, Olivieri NF, Töndury P et al. Results of Long-Term Deferiprone (Deferiprone) Therapy: A Report by the International Study Group on Oral Iron Chelators. Br J Haematol 1995; 91:224-229.

G. Link, A. Pinson, and C. Hershko. Ability of the orally effective iron chelators dimethyl- and diethyl-hydroxypyrid-4-one and of deferoxamine to restore sarcolemmal thiolic enzyme activity in iron-loaded heart cells. *Blood* 83 (9):2692-2697, 1994.

J. B. Porter, K. P. Hoyes, R. D. Abeysinghe, P. N. Brooks, E. R. Huehns, and R. C. Hider. Comparison of the Subacute Toxicity and Efficacy of 3-Hydroxypyridin-4-One Iron Chelators in Overloaded and Nonoverloaded Mice. *Blood* 78 (10):2727-2734, 1991.

G. R. Gale, W. H. Litchenberg, A. B. Smith, P. K. Singh, R. A. Campbell, and M. M. Jones. Comparative iron mobilizing actions of deferoxamine, 1,2- dimethyl-3-hydroxypyrid-4-one, and pyridoxal isonicotinoyl hydrazone in iron hydroxamate-loaded mice. *Res.Commun.Chem.Pathol. Pharmacol.* 73 (3):299-313, 1991.

C. Hershko, G. Link, A. Pinson, H. H. Peter, P. Dobbin, and R. C. Hider. Iron Mobilization From Myocardial Cells by 3-Hydroxypyridin-4-One Chelators: Studies in Rat Heart Cells in Culture. *Blood* 77 (9):2049-2053, 1991.

M. van der Kraaij, H. G. Van Eijk, and J. F. Koster. Prevention of postischemic cardiac injury by the orally active iron chelator 1,2-dimethyl-3-hydroxy-4-pyridone (L1) and the antioxidant (+)-cyanidanol-3. *Circulation* 80 (1):158-164, 1989.

Y. Aydinok, G. Nisli, K. Kavakli, C. Coker, M. Kantar, and N. Cetingul. Sequential use of deferiprone and desferrioxamine in primary school children with thalassaemia major in Turkey. *Acta Haematol.* 102 (1):17-21, 1999.

G. Faa and G. Crisponi. Iron chelating agents in clinical practice. *Coordination Chemistry Reviews* 184:291-310, 1999.

D. Kaul and S. Venkataram. Sustained release tablet formulation for a new iron chelator. *Drug Dev.Indust.Pharm.* 18 (9):1023-1035, 1992.

M. A. Barradas, J. Y. Jeremey, G. J. Kontoghiorghes, D. P. Mikhailidis, A. V. Hoffbrand, and P. Dandona. Iron chelators inhibit human platelet aggregation, thromboxane A2 synthesis and lipoxygenase activity. *FEBS Lett.* 245 (1,2):105-109, 1989.

Maria Stearns.Drug for Iron Overload Passes Major Safety Hurdle; May Benefit Patients with Thalassemia and Other Blood Disorders. *1995-2000 ScienceDaily Magazine.*

Nancy F. Olivieri and Gary M. Brittenham. Long-Term Trials of Deferiprone in Cooley's Anemia. *The Departments of Medicine and Pediatrics The Hospital for Sick Children, Division of Hematology, University of Toronto, Canada (N.F.O.)* Sep. 27, 1999.

N. F. Olivieri and G. Brittenham. Long-Term Trials of Deferiprone in Cooley's Anemia. *Ann.N.Y.Acad.Sci.* 80:217-222, 1998.

Kontoghiorghes GJ, Aldouri MA, Sheppard L, Hoffbrand AV. 1,2-Dimethyl-3-hydroxypyrid-4-one, an orally active chelator for treatment of iron overload. Lancet. Jun. 6, 1987;1(8545):1294-5.

Nathan DG. An orally active iron chelator. N Engl J Med. Apr. 6, 1995;332(14):953-4.

Olivieri NF, Brittenham GM, Matsui D, Berkovitch M, Blendis LM, Cameron RG, McClelland RA, Liu PP, Templeton DM, Koren G. Iron-chelation therapy with oral deferiprone in patients with thalassemia major. N Engl J Med. Apr. 6, 1995;332(14):918-22.

Biochimica et biophysica acta molecular basis of disease. v1500 n3 (Mar. 17, 2000) : p. 342-348. (Please note this reference is the same as *Biochimica et biophysica acta molecular basis of disease*; V.1500; No. 3; Mar. 17, 2000; pp. 342-348—(Reference 59)).

Cohen AR, Martin MB. Iron chelation with oral deferiprone in patients with thalassemia. N Engl J Med. Dec. 3, 1998;339(23):1713-4.

Grady RW, Giardina PJ. Iron chelation with oral deferiprone in patients with thalassemia. N Engl J Med. Dec. 3, 1998;339(23):1712-3.

Wonke B, Telfer P, Hoffbrand AV. Iron chelation with oral deferiprone in patients with thalassemia. N Engl J Med. Dec. 3, 1998;339(23):1712.

Stella M, Pinzello G, Maggio A. Iron chelation with oral deferiprone in patients with thalassemia. N Engl J Med. Dec. 3, 1998;339(23):1712.

Callea F. Iron chelation with oral deferiprone in patients with thalassemia. N Engl J Med. Dec. 3, 1998;339(23):1710-1.

Tricta F, Spino M. Iron chelation with oral deferiprone in patients with thalassemia. N Engl J Med. Dec. 3, 1998;339(23):1710.

Hershko C., Link G., and Ioav C.. Pathophysiology of Iron Overload. *Ann.N.Y.Acad.Sci.* 850:191-201, 1998.

Mumby, S., Chaturvedi, R.R., Brierley, J., Lincoln, C., Petros, A., Redington, A.N., Gutteridge, J.M.C.. Iron overload in paediatrics undergoing cardiopulmonary bypass. Biochimica et biophysica acta molecular basis of disease: v1500 n3 (Mar. 17, 2000): p. 342-348.

Y. Tung, F. J. Farrell, T. M. McCashland, R. G. Gish, B. R. Bacon, E. B. Keeffe, and K. V. Kowdley. Long-term follow-up after liver transplantation in patients with hepatic iron overload. *Liver Transpl.Surg.* 5:369-374, 1999.

Telfer PT, Prestcott E, Hoden S, Walker M, Hoffbrand AV, Wonke B. Hepatic iron concentration combined with long-term monitoring of serum ferritin to predict complicaitons of iron overload in thalassaemia major [In Process Citation]. Br J Haematol 2000; 110(4):971-977.

Wonke B, Anderson L, Pennell D.J. Iron Chelation Treatment Based on Magnetic Resonance Imaging (MRI) in B-Thalassaemia Major. [Abstract] 11th International Conference on Oral Chelation, Catania, Italy, pp. 61-65, 2001.

Diav-Citrin et al., 1997, Oral iron chelation with Deferiprone, Clinics of North America, (Feb. 1997) 44 (1) 235-47. Ref. 75,XP001030553.

Gabriella Link et al., Cardioprotective effect of α-tocopherol, ascorbate, deferoxamine, and deferiprone: Mitochondrial function in cultered, iron-loaded heart cells, J. Lab Clin. Med., 133(2), p. 179-183 (1999).

B. Wonke et al., Combined Therapy with Deferiprone and Desferrioxamine, British Journal of Haematology, 103, p. 361-183 (1998).

Orna Diav-Citrin et al., Oral Iron Chelation with Deferprone, New Frontiers in Pediatric Drug Therapy, 44(1) p. 235-247 (1997.

* cited by examiner

CARDIAC FUNCTION IN PATIENTS WITH THALASSEMIA MAJOR
TREATED WITH DEFERIPRONE OR DEFEROXAMINE
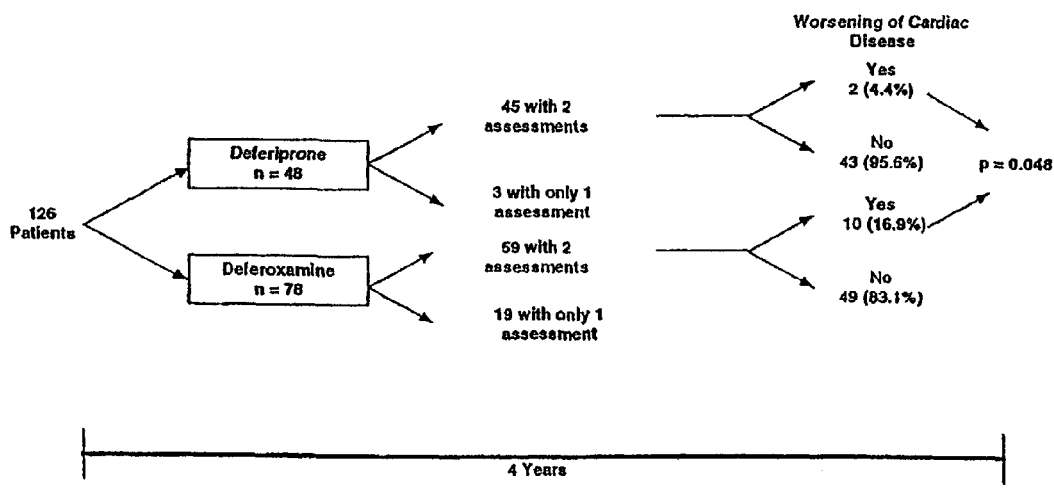
Figure 1.
Figure 2.
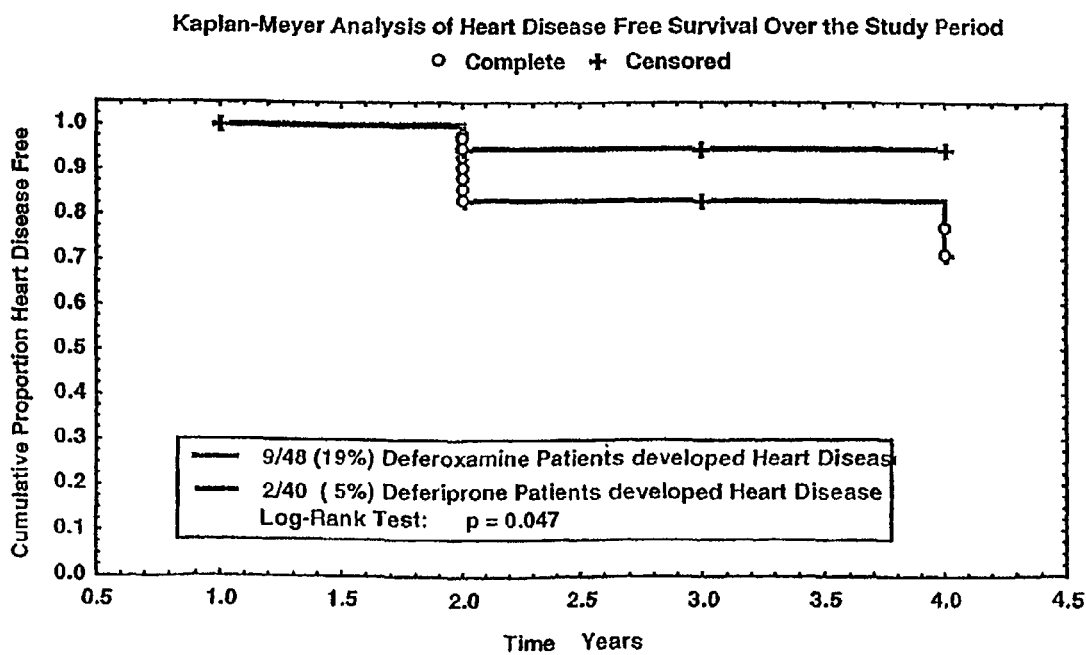

USE FOR DEFERIPRONE

This Application is a National Phase Entry Application of PCT claiming priority from Application No. PCT/CA01/00956 filed Jun. 28, 2001.

FIELD OF INVENTION

The invention relates to the use of deferiprone for the prevention/stabilization/reduction of the risk of heart disease, such as heart failure, in patients having an iron overload condition such as is found in those suffering from for example, thalassemia, hemochromatosis, and myelodysplasia, and corresponding methods of treatment involving deferiprone therefor.

BACKGROUND OF THE INVENTION

Although reference is made in the following discussion to thalassemia specifically, the invention is not intended to be interpreted as limited only to the treatment thereof. Any chronic iron overload condition would benefit from treatment by utilizing the method described herein as well as the other aspects of the invention. For example, those suffering from hemochromatosis and transfused sickle cell anemia would also benefit.

Thalassemia, among other afflictions, must be treated by regular transfusions of red blood cells in order to extend the life of the patient. However, transfusions create a widespread iron overload in the patient. Iron overload is dangerous since the excessive iron can cause toxic degenerative changes in the heart, liver and endocrine organs.

While blood transfusions constitute the major source of increased iron load, having about 1 mg of iron per ml of transfused red blood cells, increased iron absorption from the gastrointestinal tract can be observed in some diseases and also cause iron overload. Typically, only 1 mg of the dietary iron is absorbed per day. However, some conditions such as thalassemia, dyserythropoietic anemias, sideroblastic anemias, and hereditary hemochromatosis are associated with increased absorption of dietary iron. However, only 1 mg of iron is lost each day through sloughing of cells from skin and mucosal surfaces and the body does not have any organ that can perform the role of regulating the iron excretion in conditions of iron overload. Consequently, increased dietary iron absorption can also lead to iron overload and iron-induced organ toxicity, the most serious of which is heart damage. Thus, even without blood transfusions, conditions such as thalassemia, or hemochromatosis lead to increased body levels of iron, resulting in iron toxicity and eventually heart damage.

Iron chelators are drugs that enhance the iron excretion. Iron overload is most often treated by the use of the iron chelator desferrioxamine. However, because desferrioxamine is not effective when given orally, it has to be given by a parenteral route. To be clinically effective, relatively large amounts of desferrioxamine are required to be infused daily for 8 to 12 hours and this regime has to be maintained for the life span of these patients. Due to the obvious difficulties associated with such a regime, an extensive amount of research has been directed towards the development of alternative iron chelators.

Recently another iron chelator, deferiprone by oral administration, has been used successfully for removal of iron in thalassemia patients who could not comply with desferrioxamine. While patient compliance is greater with deferiprone, it is not more effective than desferrioxamine in generally removing iron from the body. In some patients deferiprone is known to produce agranulocytoisis, which is a sudden decline in white blood cells in the body. Therefore, deferiprone has been approved in Europe for use in patients with thalassemia major for whom desferrioxamine is contraindicated or who demonstrate serious toxicity concerns with desferrioxamine therapy. According to regulatory bodies, desferrioxamine is currently the agent of choice.

Children who have untreated thalassemia generally die in the first decade of life from anemia and septicemia. When palliative transfusions are introduced, children live into their late teens, but eventually succumb to heart failure if iron overload is not treated. With the introduction of frequent chronic transfusion therapy and the use of subcutaneous desferrioxamine, most children are now surviving into adulthood. However, many still die before 30 years of age, most from heart failure.

Since there is no question that desferrioxamine can eliminate iron from the body, thus reducing the total body iron load, there are 2 possible reasons why there remains a high level of premature cardiac deaths in desferrioxamine treated patients: one is that patients do not take adequate amounts of the injectable chelator, and the other is that, while it removes iron from the liver and possibly the blood, its effect on the heart are secondary, not specific for this organ.

The number of patients who are compliant, with this therapy is limited since the use of desferrioxamine normally requires the use of an infusion pump for 8 to 12 hours, 5–7 days a week as long as patients continue to receive regular blood transfusions. This is a rigorous and uncomfortable treatment regime and many patients cannot or will not comply, which results in an increased iron load and iron toxicity in various organs, including the heart.

However, it is apparent that this is not, the only reason that thalassemia patients receiving desferrioxamine therapy develop iron-induced heart disease. Three separate techniques are generally employed in the assessment of iron overload: measurement of serum ferritin concentrations; measurement of hepatic iron concentrations by chemical means following a liver biopsy; and assessment of iron concentrations in the liver or heart or other organs by physical devices, such as SQUID (super quantum interference device) and MRI (magnetic imaging resonance). The lack of adequate compliance with injectable desferrioxamine leads to a generalized increased iron overload as revealed by increases in iron concentrations assessed by the above methods, and thus also to increased levels of iron in the heart. However, data now reveal that iron-induced heart disease occurs even in patients who are compliant with desferrioxamine, and even some of those who do not have high levels of total body iron as assessed by serum ferritin or liver iron concentrations. It has thus become evident that lowering of the total body iron alone is insufficient to protect against iron-induced heart damage.

There exists therefore a long felt need to improve the life expectancy of those patients who normally develop an iron overload condition, for example thalassemia patients, who are at risk of developing or who have developed cardiac disease, and to delay the onset of heart failure in the patient as long as possible. This need also applies to others suffering from conditions of chronic iron overload to for example those secondary to blood transfusions or those associated with increased dietary iron absorption. Applicant is aware of the following technical literature which discusses the clinical use of chelating agents in conditions of chronic iron overload. These references are referred to in the detailed description of the invention.

List of References

1. Gabutti V, Piga A. Results of Long-Term Iron-Chelaing Therapy. Acta Haematol 1996; 95:26–36.
2. Wolfe L C, Olivieri N F, Sallan D, Colan S, Rose V, Propper R D et al. Prevention of cardiac disease by subcutaneous desferrioxamine in patients with thalassemia major. N Engl J Med 1985; 312(25): 1600–1603.
3. Aldouri M A, Wonke B. Hoffbrand A V, Flynn D M, Ward S E, Agnew J E et al. High Incidence of Cardiomyopathy in Beta-Thalassemia Patients Receiving Regular Transfusion and Iron Chelation: Reversal by lntensified Chelation. Acta Haematol 1990; 84:113–117.
4. Brittenham G M, Griffith P M, Noruis A W, McLaren C E, Young N S, Tucker E E et al. Efficacy of Desferrioxamine in Preventing Complications of Iron Overload in Patients with Thalassemia Major. N Engl J Med 1994; 331(9):567–573.
5. Giardina P J V, Ehlers K H, Engle M A, Grady R W, Hilgartner M W. The Effect of Subcutaneous Desferrioxamine on the Cardiac Profile of Thalassemia Major: A Five-Year Study. Ann N Y Acad Sd 1985; 445:282–292.
6. Borgna-Pignatti C, Rugologgo S, DeStefano P, Piga A, et al. Survival and Disease Complications in Thalassemia Major. Ann N Y Acad Sci 1998; 850:227–231.
7. Olivieri N F, Nathan D G, MacMillan J H, Wayne A S, Liu P, McGee A et al. Survival in Medically Treated Patients with Homozygous Beta-Thalassemia. N Engl J Med 1994; 331(9):574–578.
8. Addis A, Loebstein R, Koren G, Einarson T R. Meta-analytic review of the clinical effectiveness of oral deferiprone (Deferiprone). Eur J Clin Pharmacol 1999; 55:1–6.
9. Grady R W, Hilgartner M W, Giardina P J V. Deferiprone: Its Effectiveness Relative to that of Desferrioxamine. 6th International Conference on Thalassemia and the Haemoglobinopathies, Abstract #2. 1997.
10. Olivieri N F, Brittenham G M, Armstrong S A M, Basran R K, Daneman R, Daneman N et al. First Prospective Randomized Trial of the Iron Chelators Deferiprone (Deferiprone) and Deferoxamine. Blood 86[10 Suppl. 1], 249a. 1995.
11. Olivieri N F, Belluzzo N, Muraca M, MacKenzie C C, Milone S, Polsinelli K et al. Evidence of Reduction in Hepatic, Cardiac and Pituitary Iron Stores in Patients with Thalassemia Major During Long-Term Therapy with the Orally Active Iron Chelating Agent Deferiprone. Blood 84[10 Suppl. 1]109a. 1994.
12. Link G, Konijin A M, Hershko C. Cardioprotective effect of alpha-tocopherol, ascorbate, desferrioxamine, and deferiprone: mitochondrial function in cultured, iron-loaded heart cells. J Lab Clin Med 1999; 133: 179–188.
13. De Franceschi L, Shalev O, Piga A, Collell M, Olivieri O, Corrocher R et al. Deferiprone therapy in homozygous human beta-thalassemia removes erythrocyte membrane free iron and reduces KCI contransport activity. J Lab Clin Med 1999; 133:64–69.
14. Carthew P, Smith A G, Hider R C, Dorman B, Edwards R E, Francis J E. Potentiation of iron accumulation in cardiac myocytes during the treatment of iron overload in gerbils with the hydroxypridinone iron chelator CP94. Biometals 1994; 7:267–271.
15. Hider R C, Kayyli R, Evans P, Mackinnon S. The production of Hydroxyl Radicals by Deferiprone-iron compounds under physiological conditions. Blood 94[10], 406a. 1999.
16. Engle M A, Erlandson M, Smith C H. Late Cardiac Complications of Chronic, Severe, Refractory Anemia with Hemochromatosis. Circulation 1964; 30:698–705.
17. The Criteria Committee of the New York Heart Association. Nomenclature and Criteria for Diagnosis of Disease of the heart and Great Vessels. 9th ed. Boston, Mass; Little, Brown & Co; 1994:253–255.
18. Sirchia G, Zanella A. A Short Guide to the Management of Thalassemia. Thalassemia Today: the Mediterranean Experience. 1987: 635–670.
19. Berdoukas V, Bohans T. The Effect of Liver Iron on Cardiac Function. 10th International Conference on Oral Chelators in the treatment of Thalassemia and other diseases and Biomed Meeting 10, 13. 2000.
20. Hershko C, Graham G, Bates G W, Rachmilewitz E A. Non-Specific Serum ion in Thalassemia: an Abnormal Serum Iron Fraction of Potential Toxicity. Br J Haematol 1978; 40: 255–263.
21. Olivieri N F, Koren G, Matsui D, Liu P, Blendis L, Cameron R et al. Reduction of Tissue Iron Stores and Normalization of Serum Ferritin During Treatment with the Oral Iron Chelator Deferiprone in Thalassemia Intermedia. Blood 1992; 79(10):2741–2748.
22. Al-Refaie F N, Sheppard L, Nortey P, Wonke B, Hoffbrand A V. Pharmacokinetics of the Oral Iron Chelator Deferiprone (Deferiprone) in Patients with Iron Overload. Br J Haematol 1995; 89:403–408.
23. Novartis Marketing Brochure on Desferal (Desferrioxamine). 1998. Switzerland, Novartis Pharma AG.
24. Grady R W, Berdoukas V A, Rachmilewitz E A, Giardina P J. Combining Deferiprone and Desferrioxamine to optimize Chelation. 10th International Conference on Oral Chelators in the treatment of Thalassemia and other diseases and Biomed Meeting, Limassol, Cyprus Page 9. March 2000.
25. Töndury P, Zimmermann A, Nielsen P, Hirt A. Liver iron and fibrosis during long-term treatment with deferiprone in Swiss thalassaemic patients. Br. J. Haematol. 1998;101 (3):413–5.
26. Olivieri N F, Brittenham G M, McLaren C E, Templeton D M, Cameron R G, McClelland R A et al. Long-term safety and effectiveness of iron-chelation therapy with deferiprone for thalassemia major. N Engl J Med 1998; 339(7):417–423.
27. Hoffbrand A V, Al-Refaie F N, Davis B, Siritanakatkul N, Jackson B F A, Cochrane J et al. Long-Term Trial of Deferiprone in 51 Transfusion-Dependent Iron Overloaded Patients. Blood 1998; 91(1):295–300.
28. Olivieri N F, Butany J, Templeton D M, Brittenham G M. Cardiac Failure and Myocardial Fibrosis in a patient with Thalassemia Major (TM) Treated with Long-Term Deferiprone. Blood 92[10 (Suppl 1)], 532a. 1998.
29. Cohen A R, Galanello R, Piga A, DiPalma A, Vullo C, Tricta F. Safety profile of the oral iron chelator deferiprone: a multicentre study. Br J Haematol 2000; 108: 305–312.
30. Agarwal MB, Rajadhyaksha G, Munot S. Deferiprone: A report of 22 patients who have taken it for over a decade. 10th International Conference on Oral chelators in the Treatment of Thalassemia and other Diseases and Biomed Meeting, Limsol, Cyprus, Page 3. March 2000.
31. Liu P. Personal letter from Dr. Liu on reversal of the heart failure in a patient with thalassemia treated with deferiprone. May 13, 1996.

32. Ramm G A, Britton R S, Brunt E M, O'Neill R, Bacon B R. Hepatic iron overload in pathogen-free gerbils does not result in bridging fibrosis or cirrhosis. Bioiron'99, P. 327. 1999.
33. Hershko C., Link G., Konijn A. M. Relative effectiveness of desferrioxamine and deferiprone in protecting iron-loaded Gerbils from non-transferrin bound iron (NTBI) toxicity. Blood 94 (10): 422a; 1999.
34. Porter J B. Evaluation of New Iron Chelators for Clinical Use. Acta Haematol 1996; 95:13–25.
35. Al-Refaie F N, Hershko C, Hoffbrand A V, Kosaryan M, Olivieri N F, Töndury P et al. Results of Long-Term Deferiprone (Deferiprone) Therapy: A Report by the International Study Group on Oral Iron Chelators. Br J Haematol 1995; 91:224–229.
36. G. Link, A. Pinson, and C. Hershko. Ability of the orally effective iron chelators dimethyl- and diethyl-hydroxypyrid4-one and of deferoxamine to restore sarcolemmal thiolic enzyme activity in iron-loaded heart cells. *Blood* 83 (9):2692–2697, 1994.
37. J. B. Porter, K P. Hoyes, R. D. Abeysinghe, P. N. Brooks, E. R. Huehns, and R. C. Hider. Comparison of the Subacute Toxicity and Efficacy of 3Hydroxypyridin-4-One Iron Chelators in Overloaded and Nonoverloaded Mice. *Blood* 78 (10):2727–2734, 1991.
38. G. R. Gale, W. H. Litchenberg, A. B. Smith, P. K. Singh, R. A. Campbell, and M. M. Jones. Comparative iron mobilizing actions of deferoxamine, 1,2- dimethl-3hydroxypyrid-4-one, and pyridoxal isonicotinoyl hydrazone in iron hydroxamate-loaded mice. *Res.Commun.Chem.Pathol.Pharmacol*. 73 (3):299–313, 1991.
39. C. Hershko, G. Link, A. Pinson, H. H. Peter, P. Dobbin, and R. C. Hider. Iron Mobilization From Myocardial Cells by 3-Hydroxypyridin-4-One Chelators: Studies in Rat Heart Cells in Culture. *Blood* 77 (9):2049–2053, 1991.
40. M. van der Kraaij, H. G. Van Eijk, and J. F. Koster. Prevention of postischemic cardiac injury by the orally active iron chelator 1,2-dimethyl-3hydroxy-4-pyridone (L1) and the antioxidant (+)-cyanidanol-3. *Circulation* 80 (1):158–164, 1989.
41. Y. Aydinok, G. Nisli, K. Kavakli, C. Coker, M. Kantar, and N. Cetingul. Sequential use of deferiprone and desferrioxamine in primary school children with thalassaemia major in Turkey. *Acta Haematol*. 102 (1):17–21, 1999.
42. G. Faa and G. Crisponi. Iron chelating agents in clinical practice. *Coordination Chemistry Reviews* 184:291–310, 1999.
43. D. Kaul and S. Venkataram. Sustained release tablet formulation for a new iron chelator. *Drug Dev.Indust.Pharm*. 18 (9):1023–1035, 1992.
44. M. A. Barradas, J. Y. Jeremy, G. J. Kontoiorghes, D. P. Mikhailidis, A. V. Hofibrand, and P. Dandona. Iron chelators inhibit human platelet aggregation, thromboxane A2 synthesis and lipoxygenase activity. *FEBS Lett*. 245 (1,2): 105–109, 1989.
45. Maria Stearns.Drug for Iron Overload Passes Major Safety Hurdle; May Benefit Patients wit Thalassemia and Other Blood Disorders. 1995–2000 *ScienceDaily Magazine*.
46. Nancy F. Olivieri and Gary M. Brittenham. Long-Term Trials of Deferiprone in Cooley's Anemia. *The Departments of Medicine and Pediatrics The Hospital for Sick Children, Division of Hematology, University of Toronto, Canada* (N.F.O.) Sep. 27, 1999.
47. N. F. Olivieri and G. Brittenham. Long-Term Trials of Deferiprone in Cooley's Anemia. *Ann.N.Y.Acad.Sci*. 80:217–222, 1998.
48. Kontogbiorghes G J, Aldouri M A, Sheppard L, Hoffbrand A V. 1,2-Dimethyl-3-hydroxypyrid-4-one, an orally active Motor for treatment of iron overload. Lancet. 1987 Jun. 6;1(8545):1294–5
49. Nathan D G. An orally active iron chelator. N Engl J Med. 1995 Apr. 6;332(14):953–4.
50. Olivieri N F, Brittenham G M, Matsui D, Berkovitch M, Blendis L M, Cameron R G, McClelland R A, Liu P P, Templeton D M, Koren G. Iron-chelation therapy with oral deferiprone in patients with thalassemia major. N engl J Med. 1995 Apr. 6;332(14):918–22.
51. Biochimica et biophysica acta molecular basis of disease v1500 n3 (Mar. 17, 2000): p342–348
52. Cohen A R, Martin M B. Iron chelation with oral deferiprone in patients with thalassemia. N Engl J Med. 1998 Dec. 3;339(23):1713–4.
53. Grady R W, Giardina P J. Iron chelation with oral deferiprone in patients with thalassemia. N Engl J Med. 1998 Dec. 3;339(23):1712–3.
54. Wonke B, Telfer P, Hoffbrand A V. Iron chelation with oral deferiprone in patients with thalassemia. N Engl J Med. 1998 Dec. 3;339(23):1712.
55. Stella M, Pinzello G, Maggio A. Iron chelation with oral deferiprone in patients with thalassemia. N Engl J Med. 1998 Dec. 3;339(23):1712.
56. Callea F. Iron chelation with oral deferiprone in patients with thalassemia. N Engl J Med. 1998 Dec. 3;339(23): 1710–1.
57. Tricta F, Spino M. Iron chelation with oral deferiprone in patients with thalassemia N Engl J Med. 1998 Dec. 3;339(23):1710.
58. Hershko C., link G., and Ioav C. Pathophysiology of iron Overload. Ann.N.Y.Acad.Sci. 850:191–201, 1998.
59. Mumby, S., Chaturvedi, R. R., Brierley, J., Lincoln, C., Petros, A., Redington, A. N., Gutteridge, J. M. C. Iron overload in paediatrics undergoing cardiopulmonary bypass. Biochimica et biophysica acta molecular basis of disease: v1500 n3 (Mar. 17, 2000): p342–348
60. Y. Tung, F. J. Farrell, T. M. McCashland, R. G. Gish, B. R. Bacon, E. B. Keeffe, and K. V. Kowdley. Long-term follow-up after liver transplantation in patients with hepatic iron overload. *Liver Transpl.Surg*. 5:369–374, 1999.
61. Telfer P T, Prestcott E, Hoden S, Walker M, Hoffbrand A V, Wonke B. Hepatic iron concentration combined with long-term monitoring of serum ferritin to predict complicaitons of iron overload in thalassaemia major [in Process Citation]. Br J Haematol 2000; 110(4):971–977.
62. Wonke B, Anderson L, Pennel D. J. Iron Chelation Treatment Based on Magnetic Resonance Imaging (MRI) in B-Thalassaemia Major. [Abstract] 11th International Conference on Oral Chelation, Catania, Italy, Pages 61–65, 2001.

There are more than 250 articles in the peer-reviewed literature which refer to deferiprone and 48 of these (at the time of writing) present data on the use of deferiprone in patients with iron overload. The vast majority of these references demonstrate the safety and efficacy of this drug in treating such patients, particularly those with thalassemia major. However, there is some dispute regarding the efficacy and safety of deferiprone as an oral chelating agent, emanating particularly from one article (Reference 26) and challenged by several authors in a series of letters to the editor (References 52 through 55). Although there is some debate on the relative abilities of deferiprone, at the commonly used dose of 75 mg/kg/day, to reduce the iron concentration within the liver in comparison with desferrioxamine, used at optimal doses, there is no literature that demonstrates that deferiprone has a greater cardio-protective effect than desferrioxamine, or that it might have such activity beyond its general ability to reduce the total body iron load.

The first report of the use of deferiprone to decrease elevated levels of iron in the body in humans was published in 1987, by Kontoghiorges, the discoverer of the drug (Reference 48). Following a series of positive reports from investigators in several different countries, including England; The Netherlands, Italy, India and Canada, a particularly strong publication appeared in the New England Journal of Medicine in 1995 which reported on the unequivocal long term effectiveness of deferiprone in the reduction of body iron stores, and that it should be offered to patients unwilling or unable to use desferrioxamine This had been reported previously in a scientific meeting in 1994 (reference 11).

Reference 35 by Al-Refaie et al stated that their study leaves no doubt as to deferiprone inducing a negative iron balance in thalassaemic patients. However, the reference provides that until there is a determination of the true incidence of toxicity of deferiprone, uncontrolled use of deferiprone should be discouraged.

A serious adverse effect, agranulocytoisis (a profound lowering of the white blood cell count to levels that may not protect against infection) had been reported by several authors, including those of reference No. 10 which indicates that two patients treated with deferiprone had developed agranulocytoisis. That study concluded that data should be provided to determine the long term safety and effectiveness of deferiprone, particularly with respect to agranulocytoisis. Reference 29 by Cohen et al reported on the results of a large study regarding the safety of deferiprone finding that the development of agranulocytoisis was about 1%, which is less common than previously estimated from smaller studies and case reports.

Reference 21, reported on relatively early evidence in humans for deferiprone induced reduction of iron in the liver and the heart. The reference discusses the importance of an oral iron chelating agent in contrast to the use of desferrioxamine and its painful nightly infusions. An oral chelating agent would therefore be highly desirable as concluded in this report However, in a later;article in the New England Journal of Medicine Report (1998) by the same lead author (Reference 26), it is reported that deferiprone does not adequately control body iron burden in patients with thalassemia and may even worsen iron-induced hepatic fibrosis. Reference 28, by the same lead author, reports the development of heart failure in a 23 year old patient after treatment with deferiprone. The reference provided that the patient had been treated with desferrioxamine for 15 years until 1993 when treatment with deferiprone commenced. The author of this report suggested that deferiprone may contribute to heart failure and cardiac fibrosis.

Reference 25 by Tondury et al reports on his long term treatment (up to 8 years) of thalassemic patients with deferiprone and he concluded that there was no drug-induced liver fibrosis in his patients, although he felt there was an increase in liver iron concentrations in some of these patients.

Reference 42 by Faa and Crisponi discusses problems related to the development of non-toxic oral iron chelators with particular emphasis on the usefulness and safety of deferiprone.

Iron-induced heart toxicity is thought to be due, at least in part, to the accumulation of iron in the myocytes. Therefore evidence that deferiprone removes iron from the heart would support, although not prove, the hypothesis of a cardioprotective effect for deferiprone. An early study indicated that there was no such effect, at least in a mouse model that was studied by Gale et al (reference 38) who found that none of the compounds studied, being desferrioxamine and deferiprone among others, reduced iron concentrations from the heart in their animal model. However, later, Hershko (reference 12) reported that both desferrioxamine and deferiprone were effective in removing iron from iron-loaded rat neonatal myocytes (heart cells studied in vitro). Of particular interest was the finding that, at equimolar concentrations, desferrioxamine removed more iron than deferiprone. The observation was made that both compounds were equally effective in protecting the myocytes against iron-induced damage, even though desferrioxamine removed more iron, at the concentrations used.

The findings of the above in vitro study of rat neonatal myocytes were consistent with a study in humans suggesting decreased levels of iron in the heart during deferiprone therapy, but no benefit to heart function has been previously reported in patients. The first report of an apparent reduction in the amount of iron in the heart of a patient with thalassemia, based on magnetic resonance imaging (MRI) data, was reported in 1994 (Reference 11). The second was by the same author a year later (Reference 10). However, since the MRI was considered a semi-quantitative instrument in its ability to measure cardiac iron concentrations, and since the relationship between the level of cardiac iron and iron-induced heart disease was not known, it would have been inappropriate, at that time to have connected these observations with a reduced risk of heart disease. In addition, this author subsequently hypothesized that deferiprone is toxic to the heart (Reference 28).

Another potential contributing factor to the generation of heart disease in conditions of iron overload is "non-transferrin-bound iron" (NTBI), which is believed to represent iron bound to a heterogeneous group of non-specific and/or non-protein carriers, such as citrate. Current literature suggests that high levels of NTBI may play an important role in the development of heart disease in patients with iron overload and that a reduction in these levels may decrease the risk of developing heart disease (Reference 58).

There are some very recent publications that support the discovery of the cardioprotectant effects of deferiprone, including one published a few months ago by Mumby et al (Reference 59), where the authors state, "Our data suggest that pediatric patients are at greater risk of iron overload during cardiopulmonary bypass, and that some form of iron chelation therapy may be advantageous to decrease oxidative stress." The applicant emphasizes that this suggestion by these authors does not refer to chronic iron loading in conditions such as thalassemia, but rather to a possible acute iron loading situation, of a much less magnitude than in thalassemia, that theoretically may occur during the procedure of cardio pulmonary bypass during heart surgery. Reference 40 by Dr. van der Kraaij et al noted that there may be protection by the administration of the orally active iron chelator deferiprone which may be a promising and easily accessible approach in establishing postischemic cardiac protection in patients. Another paper (Reference 13 by De Franceshchi et al), reports that deferiprone therapy can remove pathological free iron from beta-thalassemic membrane erythrocytes, irrespective of its ability to decrease total body iron. This may be indirectly related to deferiprone's cardioprotective effect as well.

Reference is made to U.S. Pat. No. 4,840,958 by Hider et al which claims a method of treatment of a patient having a toxic concentration of iron in the body comprising administering to said patient by mouth, by bowel or parenterally, an effective amount to reduce said toxic concentration of a 3-hydroxypyrid-4-one compound which in one embodiment is deferiprone. See also at column 6, line 65. Further reference is made to UK Patent 2,118,176 to Hider et al.

Finally, reference 43, by Kaul and Venkataram discusses sustained release tablet formulations for deferiprone which, as would normally be expected by those skilled in the art, include Eudragit (a Trade mark), an acrylic based polymer, and hydroxypropylmethylcelulose.

Thus while a general review of the literature reveals that deferiprone is effective in removing iron from patients who are iron loaded (not withstanding some dissenting views), it is not definitive and dear whether or not such activity would result in decreased iron-induced heart disease and in prolongation of life. Nowhere is there taught the cardio selective/preferred function of deferiprone in relation to desferrioxamine and/or other chelating agents when administered to patients having iron overload.

It is therefore an object of this invention to use deferiprone or a physiologically acceptable salt thereof for treating and/or preventing iron induced cardiac disease or cardiac complications in a patient with iron overload, such as thalassemia or the like.

It is a further object of the invention to provide a method of reversing and or preventing iron induced cardiac disease in a patient with iron overload, such as thalassemia or the like.

Further and other objects of the invention will become apparent to those skilled in the art when considering the following summary of the invention and the detailed description of preferred embodiments related thereto.

SUMMARY OF THE INVENTION

Applicants have now discovered that the use of deferiprone in effective amounts as an iron chelating agent for patients suffering from an iron overload condition such as is found in those suffering from for example, thalassemia, hemochromatosis, or the like provides for unexpected prevention/stabilization/reduction of the risk of heart disease such as heart failure and iron-induced cardiac complications. We have unexpectedly discovered that deferiprone has a cardio selective/preferred function when compared to desferrioxamine or alternative chelating agents utilized in patients suffering iron overload. We have also determined that certain benefits are realized by the administration of deferiprone in addition to desferrioxamine to patients suffering from iron overload.

Therefore according to one aspect of the invention we have provided a method of treating and or preventing iron induced cardiac disease (such as heart failure, and iron induced cardiac complications) in a patient with iron overload, such as thalassemia or the like; comprising administering to the patient a therapeutically effective amount of deferiprone or a physiologically acceptable salt thereof sufficient to treat or prevent the iron overload condition (the iron induced cardiac disease) normally associated with thalassemia or the like.

According to another aspect of the invention we have provided a novel use of deferiprone to treat or prevent iron induced cardiac disease such as heart failure and iron-induced cardiac complications in a patient with iron overload such as thalassemia or the like comprising administering to the patient a therapeutically effective amount of deferiprone or a physiologically acceptable salt thereof sufficient to treat the iron overload condition (the iron induced cardiac disease) normally associated with thalassemia or the like.

According to another aspect of the invention there is provided a novel use of deferiprone or a physiologically acceptable salt thereof for the prevention/stabilization/reduction of the risk of heart disease such as heart failure and iron induced cardiac complications in patients having an iron overload condition associated with thalassemia or the like.

According to another aspect of the invention there is provided an effective therapeutic amount of deferiprone or a physiologically acceptable salt thereof for the prevention/stabilization/reduction of the risk of heart disease such as heart failure and iron induced cardiac complications in patients having an iron overload condition such as thalassemia or the like comprising an effective amount of deferiprone or a physiologically acceptable salt thereof sufficient to treat the iron overload condition normally associated with thalassemia or the like.

According to another aspect of the invention there is provided a method of preventing/stabilizing/reducing the risk of heart disease such as heart failure and iron induced cardiac complications in patients having an iron overload condition such as thalassemia or the like comprising the administration of a therapeutically effective amount of deferiprone or a physiologically acceptable salt thereof sufficient to treat the iron overload condition normally associated with thalassemia or the like.

According to another aspect of the invention there is provided a novel use of deferiprone in the manufacture of a pharmaceutical for preventing/stabilizing/reducing the risk of heart disease such as heart failure and iron induced cardiac complications in patients having an iron overload condition such as thalassemia or the like comprising the administration of a therapeutically effective amount of deferiprone or a physiologically acceptable salt thereof sufficient to treat the iron overload condition normally associated with thalassemia or the like.

Effective amounts of deferiprone for administration according to the invention, not only removes iron from the body, as does desferrioxamine, but also is able to bind with available iron within and/or in contact with vital organs and in so doing decrease iron-induced damage to such vital organs. Applicants have discovered the administration of these effective amounts results, in said patient being less at risk of developing cardiac disease than a patient treated with desferrioxamine. The mechanism of the apparent cardioprotective effect of deferiprone may be because of its lipophilicity and low molecular weight. Therefore, deferiprone can readily cross cell-membranes and bind intracellular iron. It may be postulated that even at relatively high liver iron concentrations, deferiprone can remove iron directly from myocytes, thus lowering or preventing iron-induced damage. This has never been demonstrated for desferrioxamine.

Even though DFO reduces general iron stores in the body, it is not cardio preferential when given subcutaneously, even for those who can (85%+) comply with the difficult parenteral regimen. Applicant's best understanding is that deferiprone readily crosses membranes and binds intracellular iron. One explanation may involve its lipophilicity, low molecular weight, and neutral charge at a pH of 7.4.

According to yet another aspect of the invention there is provided a novel use of deferiprone for the prevention, treatment, or reversal of heart disease in a patient having an iron overload condition of the heart comprising administering to the patient a therapeutically effective amount of deferiprone, or a physiologically acceptable salt thereof in order to preferentially reduce the iron stores in the heart in comparison to less critical organs/tissue in the body.

According to yet another aspect of the invention there is provided a therapeutically effective amount of deferiprone or physiologically acceptable salt thereof for the prevention, treatment, or reversal of heart disease in patients having an iron overload condition of the heart comprising an effective amount of deferiprone or a physiologically acceptable salt thereof to preferentially reduce the iron stores in the heart in comparison to the iron stores in less critical organs/tissue in the body.

According to yet another aspect of the invention there is provided a novel use of deferiprone or a physiologically acceptable salt thereof in the manufacture of a pharmaceutical for the prevention, treatment or reversal of heart disease in patients having an iron overload condition of the heart comprising a therapeutically effective amount of deferiprone or a physiologically acceptable salt thereof to preferentially reduce the iron stores in the heart in comparison to the iron stores in less critical organs/tissue in the body.

According to yet another aspect of the invention there is provided a novel use of deferiprone for the treatment, prevention, or reversal of heart disease in a patient having an iron overload condition of the heart comprising administering to the patent a therapeutically effective amount of deferiprone or a physiologically acceptable salt thereof for the direct preferential reduction/removal of iron (for example—intracellular iron) stores in the heart.

According to yet another aspect of the invention there is provided a novel use of deferiprone to prevent/treat/reverse the occurrence of iron-induced cardiac disease in patients with an iron overload condition such as thalassemia or the like, comprising administering to said patient a therapeutically effective amount of deferiprone or a physiologically acceptable salt thereof, wherein deferiprone's efficacy is cardio preferential when compared with its ability to lower total iron stores in the body.

According to yet another aspect of the invention there is provided a novel method of treating/preventing/or reversing heart disease in a patient having an iron overload condition of the heart comprising administering to the patient a therapeutically effective amount of deferiprone, or a physiologically acceptable salt thereof in order to preferentially reduce the iron stores in the heart in comparison to less critical organs/tissue in the body.

According to yet another aspect of the invention there is provided a novel method of treating/preventing/or reversing heart disease in patients having an iron overload condition of the heart comprising administering to the patient a therapeutically effective amount of deferiprone or a physiologically acceptable salt thereof to preferentially reduce the iron stores in the heart in comparison to the iron stores in less critical organs/tissue in the body.

According to yet another aspect of the invention there is provided a novel method of treating/preventing/or reversing heart disease in patients having an iron overload condition of the heart comprising a therapeutically effective amount of deferiprone or a physiologically acceptable salt thereof to preferentially reduce the iron stores in the heart in comparison to the iron stores in less critical organs/tissue in the body.

According to yet another aspect of the invention there is provided a novel method of treatment, prevention, or reversal of heart disease in a patient having an iron overload condition of the heart comprising administering to the patient a therapeutically effective amount of deferiprone or a physiologically acceptable salt thereof for the direct preferential reduction/removal of iron (for example—intracellular iron) stores in the heart.

According to yet another aspect of the invention there is provided a novel method to prevent/treat/reverse the occurrence of iron-induced cardiac disease in patients with an iron overload condition such as thalassemia or the like, comprising administering to said patient a therapeutically effective amount of deferiprone or a physiologically acceptable salt thereof, wherein deferiprone's efficacy is cardio preferential when compared with its ability to lower total iron stores in the body.

Preferably the uses and methods previously described further comprise the pharmaceutical deferiprone or a physiologically acceptable salt thereof for preventing/stabilizing/reducing the risk of heart disease such as heart failure and iron induced cardiac complications in patients having an iron overload condition such as thalassemia or the like and preferably further comprises an orally administrable dosage form of deferiprone or a physiologically acceptable salt thereof with other excipients as would be understood by persons skilled in the art. Preferably the daily administration of an amount of deferiprone and physiologically acceptable salt thereof is substantially in the range of up to 150 mg/kg of body weight of the patient, or alternatively up to 125 mg/kg, or in another embodiment up to 75 mg/kg. As is known the implied body weight assumed is a 50–60 kg individual in the case of thalassemia, or otherwise a 70 kg individual. In one embodiment the administration of a dosage amount of deferiprone or a,physiologically acceptable salt thereof is preferably 25 mg/kg administered three times daily.

Preferably deferiprone is administered in a manner selected from the group of intravenously, transdermally, rectally, orally, bucally, or aurally. In a preferred embodiment deferiprone is administered orally. In one embodiment the dosage form is a sustained release formulation preferably made in accordance with the common knowledge of a man skilled in the art. By having a constant level of deferiprone in the body, we protect against the development of heart damage from non-transferrin-bound iron. Although the current formulation provides protection, blood levels fall to very low levels after about 4 hours. Thus a sustained release formulation provides a greater level of protection by providing higher blood levels throughout the dosing period.

Although compositions incorporating a liquid diluent may be used for oral administration, it is preferred to use compositions incorporating a solid carrier, for example a conventional solid carrier material such as starch, lactose, dextrin or magnesium stearate which provides a suitable oral dosage form that is stable and does not degrade. Other forms of administration other than by injection or oral administration may also be employed such as for example by the use of suppositories.

BRIEF DESCRIPTION OF THE FIGURES

The invention will now be illustrated with reference to the following Brief Description of the Figures and Detailed Description of Embodiments.

FIG. 1 is a flow chart depicting a comparison of the cardiac function of a sample population.

FIG. 2 is a Kaplan-Meier Analysis of heart disease free survival over the study period.

DETAILED DESCRIPTION OF EMBODIMENTS

Numerical Reference in this discussion is made to the, list of references listed in the background of the invention.

The efficacy of iron chelation by desferrioxamine therapy, in subjects with thalassemia major is known. Daily subcutaneous infusions of desferrioxamine has been shown to ameliorate hepatic, cardiac and endocrinological dysfunction, improve growth and sexual maturation, and prolong survival in iron-overloaded thalassemia major patients. [1,2,3,4,5] However, iron-induced cardiac disease remains a frequent cause of morbidity in patients with thalassemia and is still responsible for 70% of the deaths among those subjects.[6] A sustained reduction in iron load, as measured by the proportion of serum ferritin results below 2500 µg/L, and the ability to comply with daily infusions of desferrioxamine have been reported to be the most important factors in the survival among patients with thalassemia major.[1,7] The age at the start of chelation therapy and the hepatic iron concentration may also affect the development of cardiac disease.[4,6]

Deferiprone, (1,2-dimethyl-3-hydroxypyrid-4one), is an orally active iron chelator that has been approved for patients with thalassemia major for whom desferrioxamine is contraindicated or who present serious toxicity with desferrioxamine therapy. Results from clinical studies have demonstrated the ability of deferiprone to remove iron from the body.[8,9] It may be relatively selective in removing iron from the heart.[10,11,12] Such activity may be a function of the physicochemical properties of deferiprone, enabling it to cross cardiac cell membranes and remove excess intracellular iron directly[13], as opposed to the more generalized action of desferrioxamine which appears to decrease cardiac iron indirectly by lowering total body iron. On the other hand, concerns have been raised that some bidentate iron chelators may play a role in Fenton reactions under conditions of incomplete iron binding[14], although more recent evidence discounts this likelihood when biologically relevant in vitro systems are employed for the study of reactive oxygen species.[15] Thus, while in vivo (animal studies) and in vitro studies are helpful, data from clinical studies are necessary to evaluate the long term efficacy of deferiprone in preventing/stabilizing/reducing iron-induced cardiac disease.

Although the long-term efficacy of deferiprone has been evaluated in various clinical trials, no information is available on the long-term efficacy of deferiprone in preventing iron-induced cardiac complications or in prolonging the survival of subjects with thalassemia major.

While a prospective study comparing deferiprone-treated and untreated patients is not possible, due to ethical concerns, meaningful data has been obtained by conducting a retrospective study comparing cardiac disease and survival in deferiprone and desferrioxamine-treated patients. A preliminary analysis by us of the data from one of the centers involved in a long-term trial with deferiprone, enabled us to determine that the use of deferiprone will prevent the occurrence of iron-induced cardiac disease in patients with thalassemia major, and that protection is greater than would be predicted from its ability to lower total body iron alone.

Applicant has explored this matter in depth and herein provides insight on the prevalence and progression of cardiac disease, and on the survival of patients treated with deferiprone for 4 or more years and compares the results with those of patients treated with daily subcutaneous infusions of desferrioxamine over the same period of time. The results of this study are set out below which also draws on the previously listed literature to interpret the findings and place them in perspective.

METHODS

Study Design

The study was a single centre, retrospective analysis of medical records of the occurrence of cardiac disease and of the survival of all subjects with thalassemia major treated with deferiprone or with desferrioxamine at the Centro Microcitemie of the University of Turin since Jan. 1, 1995. The medical records were evaluated of all patients ≧5 year-old at the time of the start of the review period and who had the diagnosis of thalassemia major confirmed by laboratory tests (electrophoresis and/or DNA analysis) and clinical criteria (participant's hemoglobin and transfusion dependency). Patients with anemia other than thalassemia major, who were HIV antibody positive, or who had a history of malignancy or required radiation or chemotherapy were not included in this review.

All patients were subjected to the same transfusion regimen aimed at maintaining the pretransfusion hemoglobin levels at 9.5–10.0 g/dL and the mean hemoglobin at 12.0 g/dL. At each episode of red blood cell transfusion, each patient was interviewed and underwent clinical evaluation by a staff physician. The iron overload was determined by monthly assessment of the transfusional-iron input and by quarterly assessment of serum ferritin. Some patients also had an annual assessment of their liver iron concentration, determined by magnetic susceptometry SQUID (Hamburg, Germany) or by biochemical assay of liver biopsy samples.

In addition to the clinical evaluation and laboratory testing, patients underwent periodic cardiac examination and assessment by a cardiologist, which in addition to the physical examination included echocardiogram and 24-hour electrocardiographic Holter monitoring if indicated. Cardiac disease was classified, according to the criteria defined by the New York Heart Association [17], by a cardiologist experienced in heart problems in subjects with hemoglobinopathies and who was unaware of the chelation therapy of the patients. Worsening of the Systolic Function (SF) or the Ejection Fraction (EF) was defined as an abnormal result at the last assessment in patients with a normal result at the first assessment for the study. Improvement was defined as a normal result at the last assessment for patients with an abnormal result at the first assessment. The first cardiac assessment was considered as the baseline value for each patient. For patients with more than one echocardiograph assessment within a year of the study, the change was based on the mean of the results of that year.

Starting in 1995, a substantial proportion of subjects followed up at the center were treated with deferiprone, in clinical trials or for compassionate therapy. For these patients, deferiprone was given in a dose of 25 mg/kg of body weight, three times per day. The remaining patients had maintained therapy with desferrioxamine (20 to 60 mg/kg/day), given as a subcutaneous infusion for 8 to 12 hour, 4 to 7 days a week except for one patient. Although 2 patients in the desferrioxamine group had their chelation intensified with intravenous chelation during the period of this review, they were not excluded from the analysis.

For patients treated with desferrioxamine compliance with chelation therapy included the following at each transfusional event:
  1.0 an individual interview focused on compliance with a non-directive approach,
  2.0 the examination of infusion sites,
  3.0 the comparison of the number of infusions prescribed to the number of infusions reported by the patient,
  4.0 records of the electronic infusor Crono® (Cane S.r.I, Italy) which registers the number of infusions, and
  5.0 the pharmacy records of desferrioxamine, syringes and needles dispensed.

For patients treated orally with deferiprone, in addition to the individual interview, the compliance was assessed at each transfusional event by the electronic MEMS® cap (Medication Event Monitoring System, Ardex Ltd, Switzerland) which records the time and date of each opening of a deferiprone container. Each record of opening of a container was presumed to represent an administered dose. Compliance was also measured by monthly counts of the number of deferiprone tablets dispensed and returned. For patients whose therapy with either chelator was interrupted for more than 4 weeks during the review period, the compliance was not calculated during the interval of interruption, but calculated separately for the various treatment periods.

Blood consumption was calculated annually using a previously standardized method[18] on the basis of the net weight and hematocrit of the blood transfused, and stored in a specific computerized system.

The Institutional Review Board (IRB) of the Turin Regional Health Authority, Italy, reviewed and approved the study protocol. Consent for review of the medical charts was obtained from patients and, for those under the age of 18, from their guardians.

Statistical Analysis

To evaluate the differences at baseline between the two groups of patients that could have an impact on the occurrence of cardiac disease and/or survival, the following clinical and laboratory parameters at the start of the study period were analysed:
  1) Gender
  2) Age
  3) Age at start of chelation therapy
  4) Transfusional iron input in the year preceding the study
  5) Serum ferritin results at the initiation of the review period
  6) Percentage of patients with more than 50% of their serum ferritin results greater than 2,500 µg/L
  7) Percentage of patients with HCV antibodies
  8) Liver iron concentration during the year preceding the study period.
  9) Urinary iron excretion results in the year preceding the study
  10) Incidence of patients with cardiac disease (NYHA class I to IV) at their first cardiac assessment The following parameters were used for comparison at termination:
  1.0 Kaplan-Meier analysis of heart disease-free survival
  2.0 Transfusion iron input
  3.0 Mean of all serum ferritin results during the last year of the study
  4.0 Percentage of patients with more than 50% of their serum ferritin results greater than 2,500 µg/L during the period of the study
  5.0 Compliance with chelation
  6.0 Liver iron concentration
  7.0 Mean of all urinary iron excretion results in the last year of the study
  8.0 Incidence of patients with cardiac disease (NYHA class I to IV) at their last cardiac assessment
  9.0 Worsening or improvement of the NYHA classification Two sample t-tests or Chi-square tests, where appropriate, were used to compare the baseline characteristics of the two treatment groups.

The Kaplan-Meier analysis of heart disease free survival for patients who were disease-free (NYHA class not applicable=0) at the beginning of the review period was performed by using the procedure LIFETEST from SAS (SAS Institute, Cary, N.C.). The primary comparison of the two groups was based on the log rank test. As not all patients had a cardiac assessment at the beginning of the review period (year 0), the time for development of heart disease was calculated as the time difference between the first available NYHA class of 0 and the first occurrence of a greater than 0 NYHA class. In addition to the Kaplan-Meier analysis, the incidence of patients with a worsening of their NYHA class from the first to the last cardiac assessment was determined for, each treatment group. Chi-square test was performed to compare the incidence between the two groups. The incidence of patients with cardiac disease diagnosed at the first cardiac assessment who showed an improvement of their NYHA class during the study was determined and compared between the two treatment groups by using the Fisher's Exact test.

To evaluate the differences related to chelation therapy between the two groups of subjects, after the start of the study, 2 sample t-tests or Chi-square tests were performed to compare their transfusional iron input, serum ferritin, percentage of subjects with more than 50% of their serum ferritin data greater than 2500 μg/L during the study, compliance with chelation therapy, liver iron concentration and urinary iron excretion.

All statistical tests were two-sided with a type 1 error (α) of 0.05. SAS (version 6.12) was used for conducting all the statistical tests.

Documentation Monitoring

A review of source documentation such as clinical charts, cardiac assessment reports and laboratory slips was made. The monitoring was conducted with 100% source document verification of the critical data cardiac assessments and 10% source document verification for noncritical data (e.g. serum ferritin results). The accepted overall error rate was 0% for critical data and less than or equal to 0.5% for non critical data.

The methodology employed in this study was a retrospective analysis of well-documented data. It is important to provide as much information as possible in retrospective analysis to prevent a selection bias, if any. In keeping with this philosophy, data for all patients that met the inclusion criteria were included. Whenever a parameter was compared in the deferiprone and desferrioxamine groups, the number of subjects which were included in each group was identified. FIG. 1 provides a graphical illustration of the main comparative groups.

Results

A total of 126 patients out of the 168 patients with thalassemia major, had been treated with desferrioxamine or deferiprone for 4 or more years at the Centro di Microcitemie since Jan. 1, 1995. Six out of the 168 patients were younger than 5 years-old at the start of the review period and were not evaluated. One patient was excluded since he presented serum antibodies for HIV. Eleven additional patients were also excluded from the study because no information was available on their chelation therapy or cardiac status. The remaining 24 patients were excluded from the analysis for having not been prescribed deferiprone or desferrioxamine for at least 4 years during the review period. One patient treated with deferiprone was maintained in the analysis although he had interrupted therapy for approximately one year during the review period.

All but one of the 126 evaluated patients were regularly chelated with daily subcutaneous infusions of desferrioxamine prior to the start of the period of this review. In 1995, forty-eight of those patients had their chelation therapy switched to deferiprone (oral administration) whereas the remaining 78 were maintained with desferrioxamine. At the time of the start of the review period, hepatic iron concentration was measured by magnetic biosusceptometry SQUID (Hamburg, Germany) in 46 of the patients treated with deferiprone and in 17 of those treated with desferrioxamine. Thirty-seven of the patients switched to deferiprone also had their hepatic iron concentration measured by biochemical assay of, liver biopsy samples.

At the start of the study, both treatment groups were similar for age, gender distribution, serum ferritin values, the percentage of patients with the majority of their serum ferritin values greater than 2,500 μg/L and urinary iron excretion results during the 2 years that preceded the study, and for the amount of transfusional iron input during the previous year. Patients whose therapy was switched to deferiprone, on the average, started chelation therapy with desferrioxamine slightly earlier than patients who were maintained with desferrioxamine. However, the mean hepatic iron concentration in the group switched to deferiprone (1.5 mg/g wet weight) appeared to be higher than that of the desferrioxamine group (1.0 mg/g wet weight) at the time of the switch.

The prevalence of cardiac disease at the first assessment was similar for both groups. Table 1 summarizes the results of the assessments at the start of the study period.

TABLE 1

Comparison of deferiprone and desferrioxamine-treated patient groups at the start of the study

|  | Deferiprone (N = 48) | Desferrioxamine (N = 78) | p |
|---|---|---|---|
| Percentage female | 46 (22) | 53 (41) | 0.463 |
| Mean age ± SD (years) | 17.1 ± 3.7 | 18.8 ± 7.1 | 0.085 |
| Mean age ± SD at start of chelation therapy with desferrioxamine (years) | 4.6 ± 2.7 (48) | 6.5 ± 4.7 (76) | 0.006 |
| Mean serum ferritin ± SD (μg/L) | 2047 ± 943 (48) | 1787 ± 1425 (64) | 0.248 |
| Percentage of patients with more than 50% of their serum ferritin results > 2,500 μg/L | 25 (48) | 14 (64) | 0.142 |
| Percentage of patients positive for HCV antibodies | 87 (46) | 75 (68) | 0.119 |
| Mean transfusional iron input ± SD (mg Fe/year) | 7732 ± 1912 (47) | 6960 ± 2213 (46) | 0.076 |
| Mean DFO-induced urinary iron excretion ± SD mg Fe/day | 15.4 ± 10.5 (46) | 15.0 ± 11.0 (53) | 0.831 |
| Mean heptic iron concentration ± SD - SQUID* | 1.5 ± 0.7 (46) | 1.0 ± 0.6 (17) | 0.003 |
| Mean hepatic iron concentration ± SD - Biopsy† | 8.2 ± 5.6 (37) | Not available | — |
| Percentage of patients with cardiac disease at first assessment | 10 (5) | 14 (11) | 0.546 |

*mg Fe/g liver wet weight
†mg Fe/g liver dry weight
(N): number of patients

The mean time of follow-up was 3.9±1.4 years for patients treated with deferiprone and 4.8±0.7 years for patients treated with desferrioxamine, which represents a cumulative total of 216 and 386 patient-years of observation for the deferiprone and desferrioxamine groups respectively. The mean compliance with deferiprone was 89%±7% SD (range 66%–99%), which was similar to that of desferrioxamine at 86%±11% (54%–100%). The average prescribed dose of lo desferrioxamine during this period was 33.5±4.0 mg/kg of body weight/day (range 20 to 45).

During the review period, patients treated with deferiprone were more heavily transfused than patients treated with desferrioxamine (p=0.0001) and also presented higher annual mean serum ferritin values over the first 3 years of follow-up (p<0.05). Nevertheless, by the end of the study period, there was no significant difference in the annual mean serum ferritin values between the 2 arms of treatment. The percentage of patients who had more than 50% of their serum ferritin values above the apparent threshold for cardiac disease (2500 μg/L)[7] throughout the review period was similar between the 2 groups. The deferiprone-induced mean annual urinary iron excretion (UIE) was greater than the desferrioxamine-induced urinary iron excretion No decrease in UIE was observed overtime in either group of patients. Table 2 summarizes the results of the analysis.

TABLE 3

Patients who were cardiac disease-free at the first assessment and had cardiac disease diagnosed at a follow-up assessment during the study.

| Patient Identification | Chelation Therapy | NYHA class (years after 1st normal assessment) |
| --- | --- | --- |
| 48 | Deferiprone | 1 (2) |
| 96 | Deferiprone | 1 (2) |
| 14 | Desferrioxamine | 1 (2) |
| 20 | Desferrioxamine | 1 (4) |
| 40 | Desferrioxamine | 1 (2) |
| 61 | Desferrioxamine | 1 (2) |
| 63 | Desferrioxamine | 1 (2) |
| 76 | Desferrioxamine | 1 (4) |
| 77 | Desferrioxamine | 1 (2) |
| 101 | Desferrioxamine | 1 (2) |
| 122 | Desferrioxamine | 1 (2) |

An improvement of the NYHA cardiac disease classification was observed in 2 of the 5 (40%) deferiprone patients and in 3 of the 11 (27%) desferrioxamine patients with cardiac disease diagnosed at the first assessment. A worsening of the cardiac disease was observed in one of the 11 desferrioxamine-treated patient with previously diagnosed cardiac disease and in none of the 5 deferiprone-treated

TABLE 2

Comparison of deferiprone and desferrioxamine-treated patient groups during the study period.

|  | Deferiprone (N = 48) | Desferrioxamine (N = 78) | p |
| --- | --- | --- | --- |
| Percentage of compliance with chelation therapy | 89 ± 7 | 86 ± 11 | 0.024 |
| Mean ± SD overall transfusional iron input (mg Fe/year) | 8777 ± 1948 | 7445 ± 2103 | 0.000 |
| Mean ± SD overall urinary iron excretion (mg Fe/day) | 18.1 ± 13.2 | 15.5 ± 12.9 | 0.000 |
| Mean serum ferritin μg/L ± SD at year 4 of the review period | 2402 ± 1331 | 2050 ± 1319 | 0.153 |
| Percentage (%) of patients with more than 50% of their serum ferritin results > 2,500 μg/L during the review period | 33 | 21 | 0.139 |
| Mean ± SD hepatic iron concentration - SQUID* during the last year of the review period | 2.5 ± 1.2 (24) | 1.8 ± 1.0 (15) | 0.075 |
| Percentage (ratio) of patients with improvement of cardiac disease diagnosed at first assessment | 40 (2/5) | 27 (3/11) | 1.000 |
| Percentage (ratio) of patients with worsening of the cardiac disease | 4 (2/45) | 17 (10/59) | 0.048 |

*mg FE/g liver wet weight
(N): number of patients

Cardiac Disease

Forty-five patients from the deferiprone group and 59 patients from the desferrioxamine group had at least 2 cardiac assessments during the study period. The mean age at the start of chelation therapy with desferrioxamine of the patients who switched to deferiprone was lower than that of patients maintained on desferrioxamine (4.6±2.6 vs 7.0±5.0 years; p=0.004). The former group of patients were also younger Man the latter (17.2±3.7 vs 20.9±6.1 years; p=0.0002). On the other hand, the deferiprone group of patients appears to have started the study with a higher heptic iron concentration (1.6±0.7 vs 0.9±0.5 mgFE/g liver wet weight; p=0.0003) and were more heavily transfused than patients treated with desferrioxamine during the review period (8759±1975 vs 7622±2450 mgFE/year p=0.0001).

patients. Newly diagnosed cardiac disease occurred in 2 of the 40 (5%) deferiprone treated patients who were cardiac disease-free at the first assessment and had a second cardiac assessment during the duration of the study. Newly diagnosed cardiac disease occurred in 9 of the 48 (19%) desferrioxamine treated patients who were cardiac disease-free at the first assessment and had a second cardiac assessment during the duration of the study (Table 3). Kaplan-Meier analysis indicates a significant difference p=0.047) in the cardiac disease free survival between the two groups. Overall, a worsening of the cardiac disease was diagnosed in 2 (4%/o) deferiprone-treated patients and in 10 (17%) desferrioxamine-treated patients (p=0.048). Table 4 provides a summary of the demographics, chelation history, and iron load of the patients who had a worsening of the cardiac function during the study period.

An abnormal SF at the first ecocardiographic assessment of the study was observed in 4 patients from the deferiprone group and in 8 from the desferrioxamine group. Improvement of the SF was observed in 2 of the 4 deferiprone-patients and in 5 of the 8 desferrioxamine-treated patients. A worsening of the SF at the last assessment was observed in 2 deferiprone-treated patients and in 6 desferrioxamine-patients.

Abnormal EF at the first assessment was observed in 3 patients, 2 treated with deferiprone and the other one with desferrioxamine. All three patients presented a normalization of the EF during chelation therapy. Worsening of the EF was observed in 3 patients, all of them in the desferrioxamine group. Seven deferiprone and 16 desferrioxamine patients had at least two 24hour Holter assessments during the study period. Arrhythmia requiring medication was diagnosed in the first assessment in 4 patients, all in the desferrioxamine group of patients. No change was observed over time in the Holter assessment in any of the evaluated patients.

Two patients received intensive chelation therapy with intravenous desferrioxamine due to the severity, of iron overload during the period of the study. One of them also presented a worsening of the cardiac function during the study.

Survival

No patient treated with either deferiprone or desferrioxamine for 4 or more years died during the study period. Three months after the completion of the study period, a male patient that had been treated with desferrioxamine over the previous 5 years died of congestive heart failure. The patient was a 26 year-old at the beginning of the study period and had started chelation therapy with desferrioxamine at age 13. During the study period his overall compliance with desferrioxamine was 54% and 89% of his serum ferritin values were greater than 2500 µg/L. No information was available regarding this patient's hepatic iron concentration. The first assessment of his cardiac function for this study was done at year 2 of the review period, when it was classified as class II. The patient's cardiac function was also ascertained as class It at the subsequent cardiac assessment during the study period.

One patient with thalassemia major who had not received either deferiprone or desferrioxamine for 4 or more years during the study period died at the Centro Microcitemie during that period. A 23 year old, female, unable to comply with subcutaneous infusions of desferrioxamine because of severe local reactions presented severe iron overload (mean serum ferritin=9000 µg/L; HIC by SQUID=9.6 mgFE/g liver wet weight; NYHA class IV). She developed heart disease and experienced two episodes of congestive heart failure while receiving intensive intravenous chelation therapy with desferrioxamine. On the occasion of the second episode, which was resistant to treatment, therapy with desferrioxamine was permanently discontinued due to infection of the central catheter. Heart failure continued to worsen and one month later, the patient initiated therapy with deferiprone, which was interrupted 19 days later because of pneumonia. There were no signs of neutropenia. The patient died a week later of congestive heart failure.

Discussion

Although effective iron chelation with desferrioxamine has been available for over 25 years, cardiac disease remains a frequent cause of morbidity and is still responsible for 70% of the deaths among patients with transfusion-dependent thalassemia patients.[1,6] Although poor compliance with desferrioxamine is considered a major contributing factor and survival beyond the age of 30 can be less than 20% for those patients unable to comply with more than 4 to 5 infusions of desferrioxamine per week.[1], even patients with good compliance and relatively low levels of iron in the liver, succumb to iron-induced heart disease.

This retrospective study was the first to examine the specific issue of the development and progression of cardiac disease in subjects with thalassemia major treated with deferiprone for 4 or more years, and to compare it with patients treated with the standard therapy, desferrioxamine, over the same period of time.

Cardiac disease, as defined by the heart functional capacity classification developed by the New York Heart Association, was an end point in this study and it was assessed in all of the thalassemia major patients irrespective of chelating treatment type. Data to establish the diagnosis and progression of cardiac disease were obtained from the medical records of patients, noting in particular, physical examinations, echocardiograms, and 24-hour electrocardiographic Holter assessments.

Prior to the start of the study, patients had been prescribed chelation therapy with subcutaneous infusions of desferrioxamine, on an average of 6.2 days per week. Patients were young, with a mean age <19 in both groups and well chelated, as determined by the mean serum ferritin values, and by the mean hepatic iron concentration assessed in a subgroup of them. Patients whose therapy was switched to deferiprone had started iron chelation therapy with desferrioxamine at an earlier age (4.6 years) than patients who were maintained with desferrioxamine (6.5 years). On the other hand, those assigned to deferiprone treatment appeared to be more heavily iron loaded, as indicated by the transfusional iron input (7732±1912 vs. 6960±2213 mg/Fe/year), serum ferritin concentrations (2047±943 vs. 1787±1425 µg/L) and percentage of patients with more than 50% of their serum ferritin results >2,500 µg/L (25% vs. 14%), although those differences were not statistically significant. The subgroup of deferiprone-treated patients with at least 2 cardiac assessments also started chelation therapy with desferrioxamine earlier than the subgroup of desferrioxamine-treated patients (4.6±2.6 vs 7.0±5.0 years) and were younger at the start of the study period (17.2±3.7 vs. 20.9±6.1 years). On the other hand, during the study the sub-group of patients switched to deferiprone were more heavily transfused than patients maintained on desferrioxamine 8759±1975 vs 7622±2450 mg Fe/year).

None of the patients evaluated died during the study period, which may reflect the regular iron chelation treatment for both treatment groups during the study period. One patient with cardiac disease (NYHA class II) from the desferrioxamine arm died of congestive heart failure 3 months after the completion of the study. This patient had started chelation therapy with desferrioxamine at the age of 13 and during the study period had an overall compliance with desferrioxamine of M5%. During the same period of time, 89% of his serum ferritin values were above the 2500 µg/L threshold. No information was available regarding his hepatic iron concentration. A patient that did not participate in this study because she could not comply with subcutaneous infusions of desferrioxamine due to severe local reactions died of iron-induced heart failure during the review period.

All subjects that met the entry criteria were included, even if their first cardiac assessment was completed after the initiation of the study. For those patients who had their first assessment after the start of the study, the only perceivable impact of the later assessment would have been to shorten the effective assessment period. The first cardiac assessment of the study showed that the percentage of patients with cardiac disease was similar for both groups. The last cardiac assessment revealed that the number of patients that had an improvement of the cardiac function during the review period was also similar for both groups. However, a worsening of the cardiac function, occurred more frequently in the desferrioxamine-treated patients than in those who had been switched to deferiprone, Overall a worsening of the cardiac function was diagnosed in 2 (4%) deferiprone-treated patients and in 10 (17%) desferrioxamine-treated patients (p=0.048).

The mean age at the start of the study for the 12 patients who presented a worsening of the cardiac function was 19.5±3.6 years (range 13 to 26) and their mean age at starting of chelation therapy with desferrioxamine was 5.8±2.7 years (range 3 to 12). During the study period, their mean compliance with the chelation regimen was 88%±12.7% (range 54% to 99%) and their mean serum ferritin values ranged from 260 to 9947 µg/L. (2277±1379 µg/L). Although 5 of the 12 patients had more than 50% of their serum ferritin values measured to be greater than 2500 ng/mL, before or during the study 3 patients did not present any serum ferritin value greater than this threshold during the review period. The hepatic iron concentrations of those patients with a worsening of the heart function ranged from 0.3 mg to 4.4 mg/Fe/g of liver wet weight (SQUID). The average hepatic iron concentration for those patients was 2.0 mg Fe/g of liver wet weight at the end of the study. There was no difference for any of these assessments between the patients who presented a worsening of the heart function and those who did not. Therefore even though desferrioxamine may reduce total body iron stores, some patients remain unprotected against iron-induced cardiac damage.

These data illustrate that development of cardiac disease in this cohort of transfused thalassemia patients could not have been predicted based upon serum ferritin values or liver iron concentrations. While it may be generally true that the greater the total iron body load, the greater the risk of developing iron-induced cardiac disease, no specific value of iron load was predictive of cardiac disease in those patients. These data support a recent study in 58 transfusion-dependent thalassemia patients where no correlation was observed between hepatic iron concentrations and cardiac function.[19].

Conclusions

The finding of this study is that patients maintained with the desferrioxamine treatment appear to be 4-fold more likely (p=0.048) to develop a worsening of their cardiac status than those who were treated with deferiprone over the same period of time. The difference does not appear to be related to a lack of compliance during the review period in the desferrioxamine treated group. In fact, only one of the ten desferrioxamine-treated patients who presented a worsening of the heart function had a compliance rate <85%. Similarly, many of these patients were "well-chelated" based upon standard measures of total body iron, illustrating that the cardio-protective mechanism of deferiprone goes beyond simple chelation.

Other actors, such as the cardiac iron load or the presence of non-transferrin-bound iron (NTBI) may also play a role in the development of cardiac disease in patients with iron overload.[20]

In retrospect, results from previous clinical studies have generally suggested without clear conclusions, and not proving, that deferiprone can remove iron from the iron-overloaded heart.[10,11,21] Monitoring of iron deposition in the heart through MRI assessments of 23 patients treated with deferiprone for over one year showed an increase of the T2 relaxation time, consistent with a reduction in cardiac iron, from 26.6±8.4 msec to 30.5±6.7 msec (p<0.005) (normal 32 msec).[11] MRI assessments during a randomized trial revealed that after a mean treatment period of 22 months, (range 18 to 23 months) there was a significant improvement in $T_2$ relaxation time in deferiprone-treated patients, but no change in desferrioxamine-treated patients.[10] These MRI data support the findings of the present study, both for deferiprone and for desferrioxamine.

A recent publication by Hershko et al demonstrated that 100 µM of desferrioxamine or deferiprone exhibited equal cardio-protective effects against iron-induced damage in neonatal rat myocytes.[12] However, these concentrations are not clinically relevant for desferrioxamine. Although a serum concentration of 100 µM for deferiprone can occur with the administration of a single 25 mg/kg dose[22], the serum concentration of desferrioxamine in patients receiving 40 mg/kg/day is usually less than 10 µM.[23]. Since the desferrioxamine concentrations used in the myocyte study were more than 10fold the expected serum concentrations, the in vivo cardioprotective effect of this chelator would be expected to be less than that of deferiprone, but not four times less protective placing the patient at a 4-fold greater likelihood of developing a worsening of their cardiac status with desferrioxamine.

The mechanism of the apparent cardio-protective effect of deferiprone may be because of its lipophilicity and low molecular weight. Therefore, deferiprone can readily cross cell-membranes and bind intracellular iron.[13] It may be postulated that even at relatively high liver iron concentrations, deferiprone can remove iron directly from myocytes, thus lowering or preventing iron-induced damage. This has never been demonstrated for desferrioxamine.

Another factor may be related to the different pharmacokinetic characteristics of deferiprone and desferrioxamine when these drugs are given at standard doses, as in the present study. For example, deferiprone at 25 mg/kg, produces peak concentrations of approximately 100 µM with serum concentrations declining to about 10 µM in 6 hours, and this pattern is repeated three times daily, seven days a week. On the other hand, desferrioxamine at 40 mg/kg achieves concentrations of only 5–10 µM and only for the duration of the infusion (8–12 hours/day, 5–7 days per week). The long periods of time without the presence of an iron chelator may have a profound effect on the generation of iron-induced activity within myocytes and through non-transferrin bound iron. These explanations provide a potential basis for understanding the difference in response to the two chelators, which, as noted by Grady at. al. probably represent compounds with access to different iron pools.[24]

The successful reversal by deferiprone of the iron-induced congestive heart failure in a patient participating in the study provides evidence for the cardio-protective effect of this iron chelator.[31]

Early reports raised concerns about the potential role of some iron chelators in promoting Penton reactions under conditions of incomplete iron binding.[14] However, a recent publication indicates that under physiological conditions there is virtually no generation of free radical damage and no more than would be expected in the control situation.[15] In addition, the toxicity that was observed with the experimental compound CP94 in gerbils, which was the basis for the hypothesis that some iron chelators may exacerbate iron toxicity, employed a defective animal model. Recently it has been shown that many of these animals have infections, but that in the absence of infection, iron does not induce liver fibrosis[32], leading to the conclusion that the infection of the animals not the use of the chelator under investigation, CP94, was responsible for the fibrosis, and this has been confirmed in a subsequent study using deferiprone in disease-free gerbils.[33]

In summary, due to scarcity of an appropriate animal model for predicting the human response to iron chelators, the results obtained in animal studies should be interpreted and have been interpreted herein with caution. The extensive clinical experience acquired during the long-term use of deferiprone by patients with thalassemia major greatly exceeds the value of the results observed in any short-term animal studies.

Clinical trials of deferiprone demonstrated that a dose of 75 mg/kg of body weight/day can control the progression of iron overload in patients with transfusion-dependant thalassemia.[8,25,27-29,31,35] The reduction or stabilization of the patients body iron load that is achieved with the use of deferiprone would be expected to contribute to some reduction on the incidence of cardiac disease, simply due to a decrease in the overall body iron load. This study has confirmed that conclusion, but the magnitude of protection was much greater than expected when measured against a chelator with equal or greater iron chelating ability, leading to the teaching presented in this study of an even greater protective effect than could be expected from overall iron reduction alone. The results also teach that the use of deferiprone has a beneficial impact on the prevention of cardiac disease among transfusion-dependant thalassemia patients.

Preferably the dosage form may be a sustained release formulation made in accordance with the common knowledge of a man skilled in the art and the constituents set out in Chart A below. By having a constant level of deferiprone in the body, we protect against the development of heart damage from fluctuating levels of non-transferrin-bound iron. Although the standard formulation provides protection, blood levels fall to very low levels after about 4 hours. Thus a sustained release formulation provides a greater level of protection by providing higher blood levels throughout the dosing period. Chart A illustrates one of the formulations prepared by the applicants as an example of a sustained release formulation of deferiprone, where the active ingredient is 500 mg. Other types of sustained release formulations are possible as well.

CHART A

| DEFERIPRONE (L1) TABS AS 500 MG CORE | |
|---|---|
| Ingredient Name | Mg Per Tablet |
| Hydroxypropyl Cellulose NF | 6.0 |
| Hydroxypropyl Methylcellulose USP | 1.5 |
| Polyethylene Glycol 8000 NF | 4.5 |
| Titanium Dioxide USP | 6.0 |
| Purified Water USP | 132.0 |
| Sub-Total | 150.0 |
| Cores: | |
| Deferiprone (L1) Tabs as 500 mg Core | 600.0 |
| Total (Excluding Water) | 618.0 |

The Assignee completed other studies wherein the largest prospective clinical study ever conducted for an iron chelator was made. One hundred eighty-seven subjects with thalassemia were enrolled in this trial conducted by Drs. A. Cohen, R. Galanello, A. Piga, and V. De Sanctis in 3 centres in Italy and 1 center in the USA. Similar to what was observed in the patients discussed above in this disclosure, no heart failure occurred in any of the other study centres in patients participating in that study, treated with deferiprone for up to 5 years.

As many changes can be made to the invention without departing from the scope of the invention, it is intended that all material contained herein be interpreted as illustrative of the invention and not in a limiting sense.

TABLE 4

Demographic, chelation, and iron overload in patients with a worsening of cardiac function during the study period.

| Patient Identification No. | Chelation therapy during study period | Age at start of the study | Age at start of chelation therapy with deferoxamine | Compliance with chelation therapy | % Ferritin >2500 ng/mL during the 2 years prior the study | % Ferritin >2500 ng/mL during the study period | HIC prior to study (SQUID*/Biopsy†) | Last HIC at study (SQUID*/Biopsy†) |
|---|---|---|---|---|---|---|---|---|
| 48 | Deferiprone | 21 | 6 | 80 | 0 | 83 | 0.6/3.8 | 2.0/NA |
| 96 | Deferiprone | 17 | 4 | 98 | 25 | 37 | 1.9/5.6 | 2.3/NA |
| 14 | Deferoxamine | 26 | 12 | 86 | 75 | 37 | NA/NA | 1.1/NA |
| 20 | Deferoxamine | 24 | 9 | 89 | 100 | 92 | NA/NA | 4.4/NA |
| 40 | Deferoxamine | 22 | 7 | 96 | 0 | 77 | 0.3/NA | NA/NA |
| 50§ | Deferoxamine | 20 | 6 | 92 | 0 | 0 | NA/NA | 0.5/NA |
| 61 | Deferoxamine | 19 | 5 | 88 | 0 | 0 | 1.4/NA | 1.6/NA |
| 63 | Deferoxamine | 19 | 4 | 94 | 0 | 3 | 1.5/NA | 1.4/NA |
| 76 | Deferoxamine | 18 | 4 | 54 | 14 | 77 | NA/NA | 2.9/NA |
| 77 | Deferoxamine | 18 | 4 | 93 | 0 | 3 | NA/NA | 1.4/NA |
| 101 | Deferoxamine | 17 | 3 | 99 | 0 | 3 | NA/NA | 1.4/NA |
| 122 | Deferoxamine | 13 | 6 | 95 | 0 | 0 | 1.1/NA | 1.0/NA |

*mg Fe/g liver wet weight
†mg FE/g liver dry weight
§Cardiac disease diagnosed at the first assessment worsened during study period The embodiments of the invention in which an exclusive property or privilege is claimed are as follows:

1. A method of treating iron induced cardiac disease in a blood transfusion dependent patient experiencing an iron overload condition of the heart, said method comprising administering to the patient a therapeutically effective amount of deferiprone or a physiologically acceptable salt thereof sufficient to stabilize/reduce iron accumulation in the heart resulting from being transfusion dependent.

2. A method of treating iron loading in the heart of a blood transfusion dependent patient experiencing an iron overload condition of the heart, said method comprising administering to the transfusion dependent patient a therapeutically effective amount of deferiprone or a physiologically acceptable salt thereof sufficient to reduce further iron overload in the heart normally associated with iron induced cardiac disease.

3. A method of treating iron loading in the heart of a blood transfusion dependent patient risking iron overload of the heart, comprising the administration of a therapeutically effective amount of deferiprone or a physiologically acceptable salt thereof to the patient.

4. A method of stabilizing iron induced heart disease in blood transfusion dependent patients having iron overload, comprising the administration of a therapeutically effective amount of deferiprone or a physiologically acceptable salt thereof sufficient to treat the iron burden in the heart normally associated with iron induced cardiac disease.

5. A method of reducing the iron burden in the heart associated with iron induced heart disease in blood transfusion dependent patients having iron overload, comprising the administration of a therapeutically effective amount of deferiprone or a physiologically acceptable salt thereof sufficient to reduce the iron burden of the heart normally associated with iron induced cardiac disease.

6. A method of treating iron induced heart disease in a blood transfusion dependent patient having an iron overload condition of the heart comprising administering to the patient a therapeutically effective amount of deferiprone, or a physiologically acceptable salt thereof in order to reduce the iron stores in the heart in preference to general iron stores in the body, such as found in the liver.

7. A method of treating iron loading in the heart of blood transfusion dependent patient having an iron overload condition of the heart comprising administering to the patient a therapeutically effective amount of deferiprone or a physiologically acceptable salt thereof to chelate the iron stores in the heart in preference to general iron stores in the body, such as found in the liver.

8. A method of treating iron loading in the heart of blood transfusion dependent patient having an iron overload condition of the heart comprising administering to the patient a therapeutically effective amount of deferiprone or a physiologically acceptable salt thereof to reduce the iron stores in the heart in preference to general iron stores organs/tissue in the body, such as found in the liver.

9. A method of treatment of iron induced heart disease in a blood transfusion dependent patient having an iron overload condition of the heart comprising administering to the patient a therapeutically effective amount of deferiprone or a physiologically acceptable salt thereof for the direct reduction/removal of intracellular iron stores in the heart.

10. A method to reduce the occurrence of iron-induced cardiac disease in a blood transfusion dependent patient with an iron overload condition, comprising administering to said patient a therapeutically effective amount of deferiprone or a physiologically acceptable salt thereof, wherein deferiprone's efficacy is cardio preferential when compared with its ability to lower total iron stores in the body.

11. The method of claims 1, 2, 3, 4, 5, 6, 7, 8, 9 or 10 wherein deferiprone or a physiologically acceptable salt thereof is administered orally for treating the risk of iron induced heart disease in patients having iron overload.

12. The method of claims 1, 2, 3, 4, 5, 6, 7, 8, 9 or 10 wherein deferiprone or a physiologically acceptable salt thereof is present in an oral dosage form with other excipients.

13. The method of claims 1, 2, 3, 4, 5, 6, 7, 8, 9 or 10 wherein the administration frequency to the patient of an amount of deferiprone or a physiologically acceptable salt thereof is daily in the range of up to 150 mg per kilogram of body weight.

14. The method of claims 1, 2, 3, 4, 5, 6, 7, 8, 9 or 10 wherein the administration frequency to the patient of a dosage amount of deferiprone or a physiologically acceptable salt thereof is daily in the range of up to 125 mg per kilogram of body weight.

15. The method of claims 1, 2, 3, 4, 5, 6, 7, 8, 9 or 10 wherein the administration frequency to the patient of a dosage amount of deferiprone or a physiologically acceptable salt thereof is daily in the range of 25 mg to 75 mg per kilogram of body weight.

16. The method of claims 1, 2, 3, 4, 5, 6, 7, 8, 9 or 10 wherein deferiprone is administered in a manner selected from the group of intravenously, transdermally, rectally, orally, bucally, or aurally.

17. The method of claims 1, 2, 3, 4, 5, 6, 7, 8, 9 or 10 wherein deferiprone is administered orally.

18. The method of claims 1, 2, 3, 4, 5, 6, 7, 8, 9 or 10 wherein deferiprone or a physiologically acceptable salt thereof is in a sustained release formulation.

19. The method of claims 1, 2, 3, 4, 5, 6, 7, 8, 9 or 10 wherein deferiprone has a cardio preferred/selective function when compared to desferrioxamine or other alternative chelating agents utilized in patients suffering iron overload.

20. The method of claims 1, 2, 3, 4, 5, 6, 7, 8, 9 or 10 wherein desferrioxamine is administered in addition to deferiprone.

* * * * *

Disclaimer

7,049,328 B2 - Michael Spino, Pickering (CA); Antonio Piga, Moncalieri (IT). USE FOR DEFERIPRONE. Patent dated May 23, 2006. Disclaimer filed September 11, 2017, by the inventor.

I hereby disclaim the following complete claim 3 of said patent.

*(Official Gazette, September 6, 2022)*